United States Patent [19]

Panzica et al.

[11] Patent Number: 5,587,494

[45] Date of Patent: Dec. 24, 1996

[54] PRACTICAL, COST-EFFICIENT CHIRAL SYNTHESIS OF DIHYDROSPHINGOSINES

[75] Inventors: Raymond P. Panzica, Narragansett, R.I.; Hussein I. El Subbagh, Al-Hussnieh, Egypt; Elie Abushanab, Peace Dale, R.I.

[73] Assignee: The Board of Governors for Higher Education, State of Rhode Island and Providence Plantations, Providence, R.I.

[21] Appl. No.: 42,875

[22] Filed: Apr. 5, 1993

Related U.S. Application Data

[63] Continuation-in-part of Ser. No. 852,885, Mar. 17, 1992, abandoned.

[51] Int. Cl.⁶ .................. C07D 303/00; C07C 211/00; C07C 209/00
[52] U.S. Cl. .................. 549/512; 564/463; 564/489
[58] Field of Search .................. 549/512; 564/463, 564/489

[56] References Cited

U.S. PATENT DOCUMENTS 5,012,000  4/1991  Illig et al. .................. 564/489
5,430,169  7/1995  Boumendjel et al. .................. 558/169

OTHER PUBLICATIONS

J. Org. Chem., vol. 50, issued 1985, Roush et al, "Directed Openings of 2,3–Epoxy Alcohols via Reactions with Isocyanates: Synthesis of (+)–erythro–Dihydrosphingosine", pp. 3752–3757.

Chemical Abstracts, vol. 73, No. 23, issued 1970, Eller et al, "Synthesis of D–erythro Dihydrosphingosine", p. 299, col. 2, abstract No. 14056s, *Zh. Org. Khim.* 1970, 6(4), pp. 665–668 (Russ).

Chemical Abstracts, vol. 77, No. 30, issued 1972, Zav'yalov et al, "Synthesis of Racemic Erythro–dihydrosphingosine", p. 489, col. 1, absract No. 75357v, *Isv. Akad. Nauk* SSR, *Ser. Khim.* 1972 (6), 1445–1446 (Russ).

*Primary Examiner*—John Kight
*Assistant Examiner*—Everett White
*Attorney, Agent, or Firm*—Samuels, Gauthier, Stevens & Reppert

[57] ABSTRACT

Sphingolipids are involved in the structure of biological membranes. There is a link between sphingolipids and signal transduction. The invention relates to the stereospecific syntheses of dihidrosphingosines using certain chiral epoxides.

4 Claims, 1 Drawing Sheet

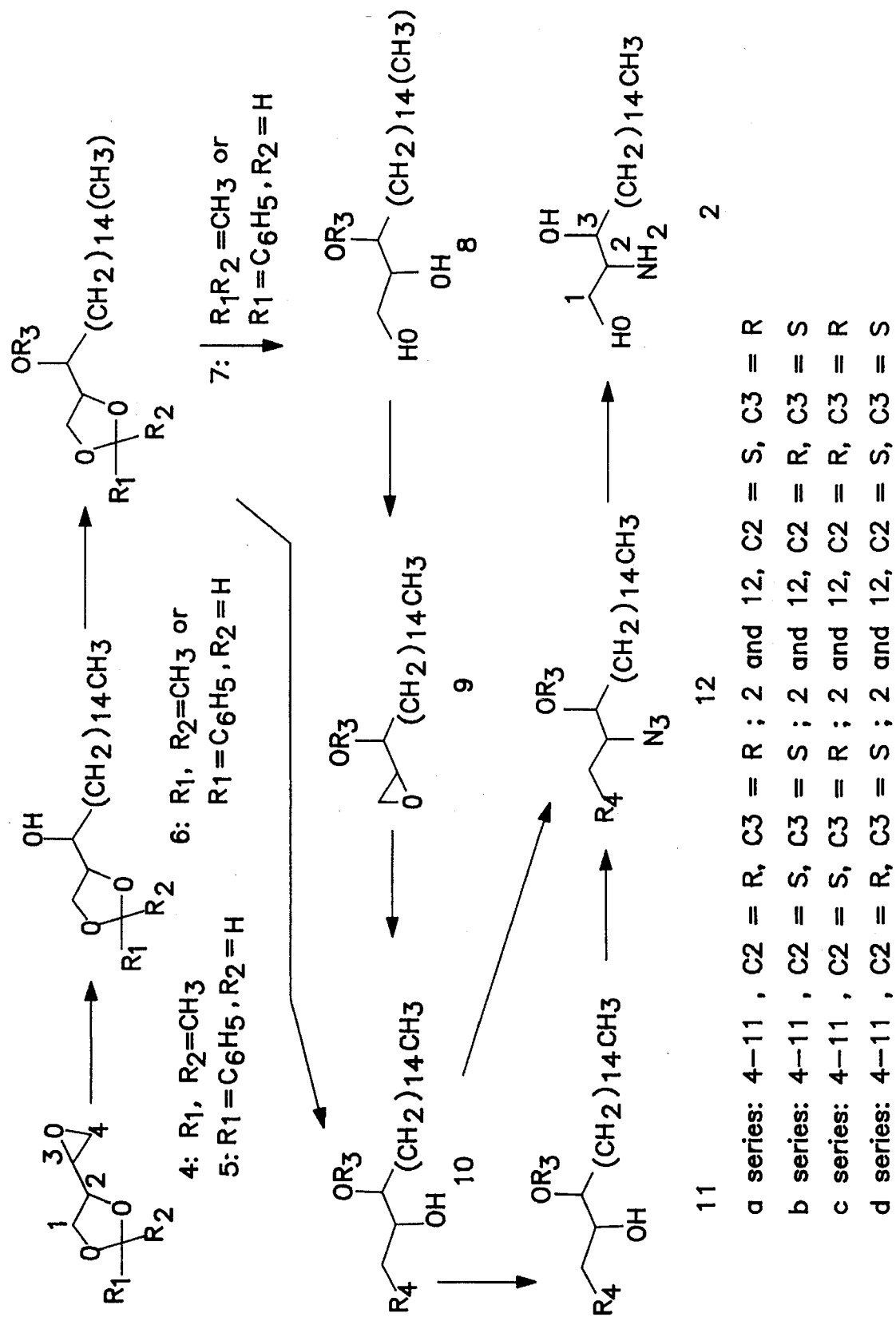

PRACTICAL, COST-EFFICIENT CHIRAL SYNTHESIS OF DIHYDROSPHINGOSINES

This is a continuation-in-part of application Ser. No. 07/852,885 filed on Mar. 17, 1992, now abandoned.

BACKGROUND AND BRIEF SUMMARY OF THE INVENTION

A variety of complex lipids are involved in the structure of biological membranes. These lipids can be classified into two categories, the glycerophospholipids and the sphingolipids. The sphingolipids or sphingoid bases, as they are commonly referred to, are natural, long-chain amino bases. They typically have a 2-amino-1,3-diol hydrophilic head and a long (usually 15-carbon), hydrophobic (lipophilic) alkyl chain. The amphiphlic nature of these biomolecules is responsible for their properties and function in the membrane, Liscovitch, M. et al, *Biochem. Parmacol.* 1991, 42, 2071–2075.

There is a link between sphingolipids and signal transduction. Shingoid bases have been shown to inhibit the protein kinase C, in vitro, Hannun, Y. et al, *J. Biol. Chem.* 1986, 261, 12604–12609, and thus the cellular responses mediated by protein kinase C, Nashizuka, Y., *Science* 1986, 223, 305–312; Bell, R. M., *Cell* 1986, 45, 631–632; Morrill, A. H., Jr. et al, *Biochim Biophys. Acta* 1989, 1010, 13–139. Sphingosine is one of the most potent inhibitors of the protein kinase C.

Recent SAR studies have revealed that inhibition is about the same with all of the major, naturally occurring long-chain bases, Hannun, Y. et al, *J. Biol. Chem.* 1986, 261, 12604–12609; Wilson, E. et al, *J. Biol. Chem.* 1986, 261, 12610–12614; and Merrill, A. H., Jr., et al, Biochemistry 1989, 28, 3138–3145; i.e., sphinganine (2, dihydrosphingosine) and 4-D-hydroxyphinganine (3, phytoshingosine). Key factors in the development of these sphingoid bases as inhibitors of the protein kinase C are: 1) they do not appear to affect most other kinases and 2) they are natural constituents of cells and tissues, Liscovitch, M. et al, *Biochem. Parmacol.* 1991, 42, 2071–2075.

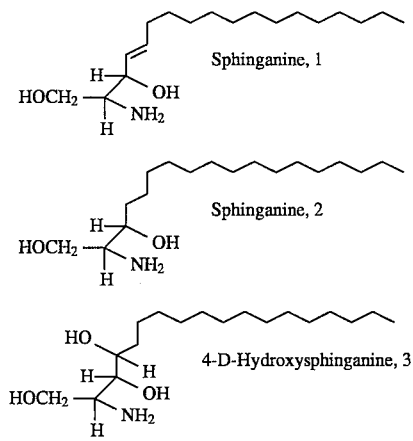

Broadly the invention comprises the stereospecific syntheses of the dihidrosphingosines, which syntheses utilize certain chiral epoxides, set forth below, which chiral epoxides have been previously described, (a) Abushanab, E., U.S. Pat. No. 4,931,575; (b) Abushanab, E. et al, *J. Org. Chem.* 1988, 53, 2598–2602; (c) Vargeese, C. et al., *J. Org. Chem.* 1990, 55, 4400–4403.

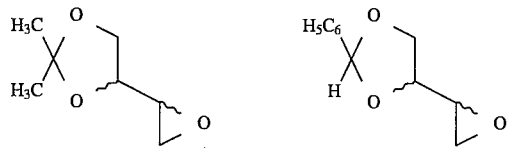

4a. 2R, 3R  
4b. 2S, 3S  
4c. 2S, 3R  
4d. 2R, 3S 5a. 2R, 3R  
5b. 2S, 3S  
5c. 2S, 3R  
5d. 2R, 3S

The syntheses or processes of the invention comprise the steps, subsequent to step 4 in the reaction scheme shown in the FIGURE. The invention embodies all four isomers, where each chiral center can be R or S of compounds 6 through 14 shown in the FIGURE.

BRIEF DESCRIPTION OF THE DRAWINGS

The FIGURE is a scheme of syntheses of all four sphinganines. A typical sequence describes the preparation of D-dihydrosphingosine (2,2S,3R-sphinganine).

DESCRIPTION OF THE PREFERRED EMBODIMENT(S)

The preferred embodiment will be described with reference to the FIGURE and to the synthesis of D-dihydrosphingosine (2S, 3R-sphinganine) with the starting compounds 4a and 5a via alternative synthetic routes.

Referring to the FIGURE, in a first synthetic route where $R_1$, $R_2 = CH_3$, (2R,3R)-3,4-Epoxy-1,2,-0-isopropylidenebutane-1,2-diol (4a) was reacted with tetradecylmagnesium chloride in tetrahydrofuran (THF) under nitrogen for 3 hours to furnish a 94% yield of (2R,3R)-1,2-0-isopropyl-deneoctadecane-1,2,3-triol (6a). Protection of the 3-ol position as a benzyl to afford 7a was accomplished in 87% yield. Alternatively, allyl alcohol can be used in place of benzyl alcohol to protect this position. The allyloxy protecting group can be easily removed under mild reductive conditions, Cichy, A. F. et al, *J. Org. Chem.* 1991, 56, 4653–4658. Opening of the acetonide with acid 8a, (97%) followed by a Mitsunobu reaction provided 9a (89%) in good yield.

Compound 9 [1,2-epoxy-3-0-benzyloctadecane-1,2,3,-triol] is an extremely versatile chiron and can be employed to synthesize a variety of "head"-modified sphinganines.

For example, treatment of 9 with dimethyl methylphosphate in the presence of butylithium and ($BF_3 \cdot OEt_2$) borontrifluoride etherate will afford the phosphonate 10. (where $R_3 = CH_2C_6H_5$ and $R_4 = CH_2P(O)(OCH_3)_2$; see the Scheme).

Nu: + 9($R_3 = CH_2C_6H_5$) $\xrightarrow[\text{THF, } BF_3.OEt_2]{\text{BuLi}}$

[$(CH_3O)_2P(O)CH_2$]

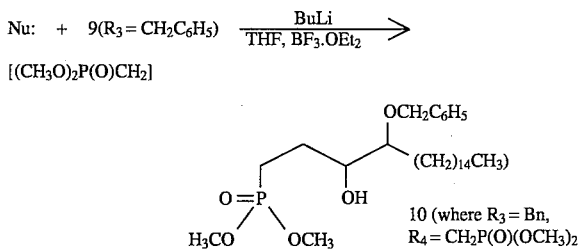

10 (where $R_3 = Bn$, $R_4 = CH_2P(O)(OCH_3)_2$

Regiospecific opening of 9a with sodium benzylate gave 10a (75%). Conversion of the 2R position to 2S was accomplished in two ways. First, 10a was tosylated to 11a and then inverted with azide ion to give 12a. A second, more direct route involved inversion using diphenylphosphorylazide under Mitsunobu conditions to give 12a in 95% yield. Reduction of the azide 12a furnished 2a which was characterized as its triacetate.

A second synthetic route employs compound 5a, where $R_1=C_6H_5$ and $R_2=H$ and shortens the process by 3–4 steps. With the exception of steps 7→10, the chemistry was identical to that illustrated in Scheme 1. Reduction of the benzylidene 7a (where $R_1=C_6H_5$, $R_2=H$) with DIBALH (diisobutylaluminum hydride) furnished 10a (where $R_3=CH_2C_6H_5$ and $R_4=OCH_2C_6H_5$) in 82% yield.

EXAMPLE

The preparation of (2R,3R)-1,2-O-Isopropylideneoctadecane-1,2,3-triol (6a, where $R_1R_2=CH_3$).

Tetradecylmagnesium chloride (65mL, 65 mmol), 1.5 mL of a catalytic solution [LiCl (0.085 g), $CuCl_2$ (0.134 g) in THF (5 mL)] and THF (100 mL) were cooled to −78° C. Compound 4a (4.6 g, 32 mmol) in THF (20 mL) was added dropwise to the cooled, stirred solution (under $N_2$). and after addition was complete the reaction was stirred for 3 hours at −78° C. The reaction mixture was allowed to warm up to room temperature and left overnight. A saturated $NH_4Cl$ solution (20 mL) was then added to the reaction mixture and stirred for 15 min. Solvents were then evaporated under reduced pressure. The resulting residue was extracted with ether, dried (anhyd. $MgSO_4$) and evaporated. The oily product was purified on silica gel using hexanes/ethylacetate (9:1, v/v) to give 6a (10.33 g, 94.47%). $[\alpha]_D^{25}+8.04$ (c 0.995, $CH_2Cl_2$); $^1H$ NMR ($CDCl_3$) δ0.85 (m, 3H), 1.0–1.6 (m, 39H), 2.0–2.4 (m, 3H), 3.3–4.1 (m, 4H). Anal. Calcd for $C_{21}H_{42}O_3O_3$: C, 73.63; H, 12,36. Found: C, 73.49; H, 12.29.

The preparation of (2R, 3R) -1,2-O-Benzylidineoctadecane-1,2,3-triol (6a, where $R_1=C_6H_5$, $R_2=H$).

Epoxide 5a (2.45 g, 12.75 mmol) was treated in the same manner as 4a for the synthesis of 6a (where $R_1R_2=CH_3$). Treatment of 5a in the presence of 1 mL of the catalytic solution in anhydrous THF (40 ml furnished 4.6 g (93%) of the title compound. Anal. calcd for $C_{25}H_{42}O_3$: C, 76.87; H, 10.84. Found: C, 76.91; H, 10.86.

The preparation of (2R, 3R) -1,2-O-Isopropylidene-3-O-benzyloctadecane-1,2,3-triol (7a, where $R_1R_2=CH_3$, $R_3=CH_2C_6H_5$).

To a stirred suspension of NaH (60%, 1.8 g, 46 mmol) in dry DMF (20 mL) was added dropwise a solution of 6a where $R_1R_2=CH_3$ (10.33 g, 30 mmol) in DMF (80 mL). The reaction was stirred at room temperature for 0.5 hours, and then benzyl bromide (5.8 g, 4.1 mL, 34 mmol) was added dropwise. Once the addition was complete, the reaction was stirred at room temperature overnight. Solvent was then removed under reduced pressure and excess NaH was decomposed by the addition of water. The product was then extracted with $CH_2Cl_2$, dried (anhyd. $MgSO_4$), and the excess solvent evaporated and the residue chromatographed on silica gel using hexanes/ethylacetate (95: 5, v/v) to give 7 (11.3 g, 86.7%). $[\alpha]_D^{25}+19.55$ (c 1.1, $CH_2Cl_2$); $^1H$ NMR ($CDCl_3$) δ0.85 (m, 3H), 1.0–1.6 (m, 32H), 1.7–1.9 (m, 2H), 3.2–4.3 (m, 4H), 4.4–4.85 (ABq, 2H, J=12Hz, $CH_2C_6H_5$), 7.25 (s, 5H, $CH_2C_6H_5$). Anal. calcd for $C_{32}H_{48}O_3$: C, 77.72; H, 11.18. Found: C, 77.63; H, 11.08.

The preparation of (2R, 3R)-1,2-O-Benzylidine-3-O-benzyloctadecane-1,2,3-triol (7a where $R_1=C_6H_5$, $R_2=H$, $R_3=CH_2C_6H_5$) .

Benzylation of 6a (where $R_1=C_6H_5$, $R_2=H$) was carried out as described for the preparation of 7a (where $R_1R_2=CH_3$). Sodium hydride (150 mg, 3.75 mmol) was reacted with 6a (975 mg, 2.50 mmol) in DMF and to the suspension was added benzyl bromide (0.45 mL; 641 mg, 3.75 mmol). Work-up of the reaction provided the title compound (960 mg, 80%). Anal. calcd for $C_{32}H_{48}O_3$: C, 79.95; H, 10.06. Found: C, 79.86; H, 9.84.

The preparation of (2R,3R)-3-O-Benzyloctadecane-1,2,3-triol (8a, where $R_3=CH_2C_6H_5$).

Compound 7a (13.75 g, 31.8 mmol) was dissolved in 95% EtOH (100 mL) and to the solution was added water (2.5 mL), concentrated hydrochloric acid (2.0 mL), and amberlite IR-130 resin (5.85 g). The reaction was stirred at room temperature for 20 hours and then the resin was removed by filtration and the filtrate concentrated in vacuo. The crude product was crystallized from hexanes to give 8a (12.1 g, 96.7%). mp 58–60° C.; $[\alpha]_D^{25}-16.5$ (c 0.825, $CH_2Cl_2$); $^1H$ NMR ($CDCl_3$) δ0.9 (m, 3H), 1.1–1.75 (m, 28H), 2.35 (br S, 2H), 3.3–3.38 (m, 4H), 4.6 (ABq, 2H, J=12 Hz, $CH_2C_6H_5$. Anal. Calcd for $C_{25}H_{44}O_3$: C, 76.48; H, 11.30. Found: C, 76.24; H, 11.49.

The preparation of 1,2-Epoxy-3-O-benzyloctadecane-1,2,3-triol (9a, where $R_3=CH_2C_6H_5$).

Triphenylphosphine (9.64 g, 37 mmol) and the diol 8a (12.1 g, 31 mmol) were dissolved in toluene ( 130 mL). Diisopropyl azodicarboxylate (7.5 g, 37 mmol) was added dropwise and the mixture was allowed to stir for 1 hour at room temperature. The solvent was removed and the residue was heated at 100° C. for 2 hours and then purified by silica gel chromatography using hexanes/ethylacetate (95:5, v/v) as eluant to give 9a (10.26 g, 89.2%); $[\alpha]_D^{25}+9.02$ (c 2.45, $CH_2Cl_2$); $^1H$ NMR ($CDCl_3$) δ0.9 (m, 3H), 1.1–1.65 (m, 28H), 2.3–2.5 (m, 1H), 2.6–2.8 (m, 1H), 2.9–3.1 (m, 2H), 4.6 (ABq, 2H, J=12 Hz, $CH_2C_6H_5$), 7.1–7.4 (m, 5H, $CH_2C_6H_5$). Anal. Calcd for $C_{25}H_{42}O_2$: C, 80.15; H, 11.30. Found: C, 80.14; H, 11.14.

The preparation of (2R,3R)-1,2-Di-O-benzyloctadecane-1,2,3-triol (10a, where $R_1R_2=CH_3$, $R_3=CH_2C_6H_5$, $R_4=OCH_2C_6H_5$).

Method A. Benzyl alcohol (15.0 mL, 144.2 mmol) in t-BuOH (80 mL) was added to a sodium hydroxide [2.0 g (50 mmol) was dissolved in water (2 mL)] solution and the mixture was heated at reflux for 0.5 hour. Compound 9a (9.2 g, 24.5 mmol) was then added and heating continued for 6 hours. The volatile solvents were removed by evaporation and the remaining aqueous layer was extracted with $CH_2Cl_2$. The organic layer was dried over anhyd. $MgSO_4$, filtered, and evaporated in vacuo. The oily residue was purified by silica gel chromatography using hexanes/ethyl acetate (95:5, v/v) to furnish 1.4 g of starting material and 10 (7.52g, 74.6%); $[\alpha]_D^{25}-6.68$ (c 1.9, $CH_2Cl_2$); $^1H$ NMR ($CDCl_3$) δ0.85 (m, 3H), 1.0–1.65 (m, 28H), 2.4 (3, 1H, J=6 Hz), 3.35–3.55 (m, 2H), 3.6–4.1 (m, 2H), 4.3–7.7 (m, 4H, 2 $CH_2C_6H_5$), 7.25 (s, 10H, $2CH_2C_6H_5$). Anal. Calcd for $C_{32}H_{50}O_3$: C, 79.62; H, 10.44. Found: C, 79.89; H, 10.18.

Method B: Compound 7a where $R_1=C_6H_5$, $R_2=H$, $R_3=CH_2C_6H_5$ (240 mg, 0.5 mmol) was dissolved in toluene (5 mL) and the stirred solution cooled to 0° C. Diisobutylaluminum hydride (DIBALH; 1.5 mL of a 1.0 M toluene solution, 3 mmol) was added to this solution and the reaction mixture was stirred 1 hour at 0° C. The reaction mixture was allowed to warm to room temperature and stirred overnight. Excess reducing agent was decomposed with a saturated $NH_4Cl$ solution and a 20% citric acid solution. Next the reaction mixture was extracted with ether and the ether layer washed with water and dried over anhyd. $MgSO_4$. The dried ether layer was filtered, evaporated under reduced pressure, and chromatographed on silica gel using hexanes/ethyl acetate (95:5, v/v). Pure 10a (200 mg, 82%) was obtained which was identical in all respects to 10a prepared from Method A.

The preparation of (2R, 3R)-1,2-Di-O-benzyl-2-O-tosyloctadecane-1,2,3-triol (11a, where $R_3$=CH$_2$C$_6$H$_5$, $R_4$=OCH$_2$C$_6$H$_5$, $R_6$=p-CH$_3$C$_6$H$_4$SO$_2$).

Compound 10a (2.0 g, 4.143 mmol) and p-toluenesulphonyl chloride (0.9 g, 4.72 mmol) was dissolved in CH$_2$Cl$_2$ (50 mL). To this solution was added pyridine (15 mL) and the reaction mixture was allowed to stir at room temperature for 24 hours. Next, water (100 mL) was added to the reaction and the organic phase separated. This phase was washed with 1N HCl (100 mL) and water (100 mL) and then dried over anhyd MgSO$_4$. After removal of the solvent, the crude product was purified by silica gel column chromatography [hexanes/ethylacetate (95:5, v/v)] to afford 0.26 g of 10a and 11a (1.1 g, 48%); $[\alpha]_D^{25}$+10.09 (c 1.64, CH$_2$Cl$_2$); $^1$H NMR (CDCl$_3$) δ0.9 (m, 3H). 1.1–1.6 (m, 28H), 2.3 (s, 3H, CH$_3$C$_6$H$_4$SO$_2$), 3.45–3.8 (m, 3H, 4.3 (s, 2H, CH$_2$C$_6$H$_5$), 4.55 (s, 2H, CH$_2$C$_6$H$_5$), 4.6–4.9 (m, 1H), 7.0–7.4 (m, 12H, 2 CH$_2$C$_6$H$_5$, CH$_3$C$_6$H$_4$SO$_2$), 7.7 (d, 2H, J=9.0 Hz, CH$_3$C$_6$H$_4$SO$_2$). Anal. Calcd for C$_{39}$H$_{56}$SO$_5$: C, 73.54; H, 8.86; S, 5.03. Found: C, 73.62; H, 8.88, S, 4.91.

The preparation of (2S, 3R)-2-Azido-1,2-di-O-benzyloctadecane-1,2,3-triol (12a, where $R_3$=CH$_2$C$_6$H$_5$, $R_4$=OCH$_2$C$_6$H$_5$).

Method A: Compound 10a (1.0 g, 2.07 mmol) was dissolved in THF (75 mL). Triphenylphosphine (0.44 g, 2.09 mmol), Diisopropyl azodicarboxylate (0.42 g, 2.08 mmol) and diphenylphosphorylo azide (0.57 g, 2.07 mmol) was added to the solution and the reaction mixture was stirred at room temperature for 24 hours. The excess solvent was then removed under reduced pressure and the resulting residue chromatographed on silica gel using hexanes/CH$_2$Cl$_2$ (7:3, v/v) to give 12a (0.994 g, 94.5%).

Method B: To a solution containing Compound 11a (1.0 g, 1.6 mmol) in DMF (20 mL) was added sodium azide (0.21 g, 3.2 mmol) and the mixture was heated at 100° for 7 hours. The reaction mixture was allowed to cool and then the solvent was removed in vacuo and the residue chromatographed as mentioned above to give 12a (0.69 g, 86.6%); $[\alpha]_D^{25}$+11.68 (c 1.9, CH$_2$CL$_2$), $^1$H NMR (CDCl$_3$) δ0.9 (m, 3H), 1.1–1.6 (m, 28H), 3.4–3.8 (m, 4H, 4.5 (s, 4H, 2 CH$_2$C$_6$H$_5$), 7.25–7.45 (m, 10H, 2 CH$_2$C$_6$H$_5$). Anal. calcd for C$_{32}$H$_{49}$N$_3$O$_2$: C, 75.69; H, 9.73; N, 8.28.

The preparation of 2, 2S,3R-Sphinganine (2). Catalytic reduction, Reist, E. J.; Christie, P. H., *J. Org. Chem.* 1970, 35, 3521–3524, of 12a leads to the title compound. 2S,3R-sphinganine was characterized by conversion to the known triacetate: mp 92°–93° C., [Lit, Reist, E. J.; Christie, P. H., *J. Org. Chem.* 1970, 35, 3521–3524, 90°–93° C.]; $[\alpha]_D^{19}$+15.7 (c =0.7, chloroform), [Lit, Reist, E. J.; Christie, P. H., *J. Org. Chem.* 1970, 35, 3521–3524, $[\alpha]_D^{19}$+16.0 (c=0.5, chloroform)].

Although described with reference to the starting compounds 4a, 5a (2R,3R) syntheses using the other R and S isomers 4b, 4c, 4d and 5b, 5c and 5d are within the scope of the invention.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described our invention what we now claim is:
1. A compound of the structure:

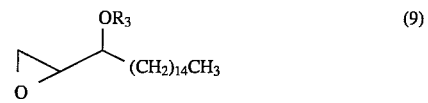

(9)

where $R_3$ equals CH$_2$C$_6$H$_5$ or

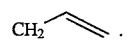

.

2. A process for the preparation of a compound of the structural formula 2

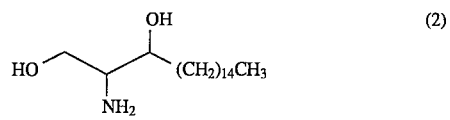

(2)

which comprises:

adding an organomagnesium composition to a compound of the structural formula 4 to form a compound of the structural formula 6.

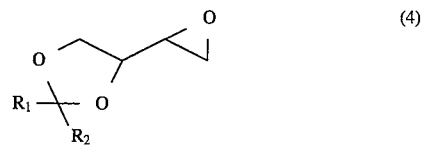

(4)

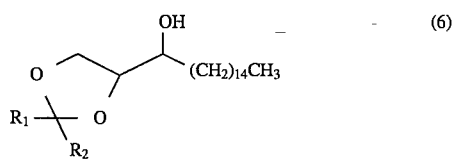

(6)

benzylating a compound of structural formula 6 to form a compound of the structural formula 7

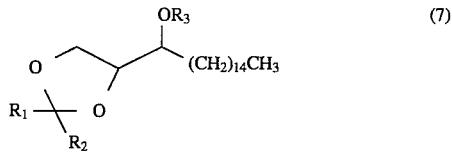

(7)

hydrolyzing 7 with acid to form a compound of the structural formula 8

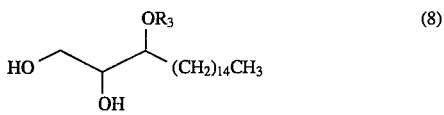

(8)

dehydrating 8 to form a compound of the structural formula 9

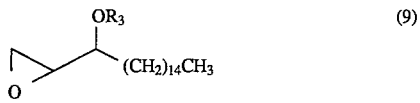

(9)

converting the epoxide of 9 to a corresponding alcohol to form a compound of the structural formula 10

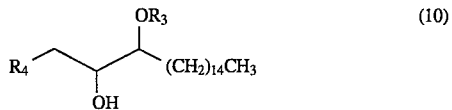

(10)

inverting 10 to form a compound of the structural formula 12

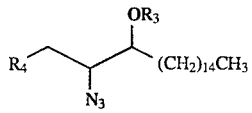 (12)

reducing 12 to form the compound 2
where $R_1, R_2$ equals $CH_3$ $R_3$ equals $Ch_2C_6H_5$ or

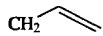

$R_4$ equals $OCH_2C_6H_5$, $OC(CH_3)_3$

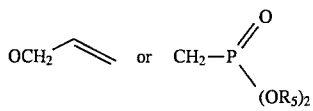

$R_5$ equal $C_nH_{2n+1}$
where
n=1, 2, or 3.

3. A process for the preparation of a compound of the structural formula 2

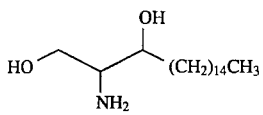 (2)

which comprises:

adding an organomagnesium composition to a compound of the structural formula 4 to form a compound of the structural formula 6

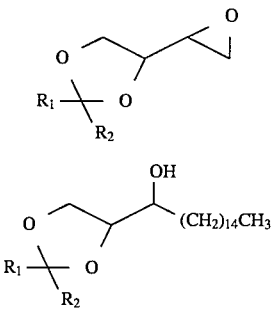 (4)

(6)

benzylating a compound of structural formula 6 to form a compound of the structural formula 7

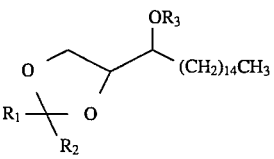 (7)

reducing 7 to form a compound of the structural formula 10

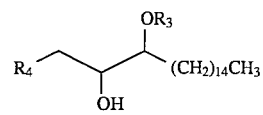 (10)

inverting 10 to form a compound of the structural formula 12

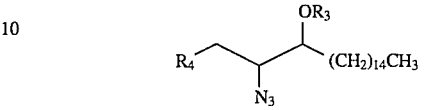 (12)

reducing 12 to form the compound 2
where $R_1$ equals $C_6H_5$ $R_2$ equals H $R_3$ equals $CH_2C_6H_5$ or

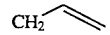

$R_4$ equals $OCH_2C_6H_5$, $OC(CH_3)_3$

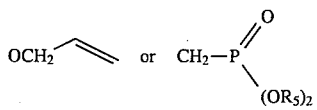

$R_5$ equal $C_nH_{2n+1}$
where
n=1, 2 or 3.

4. The method of claims 2 or 3 which comprises: tosylating 10 to form a compound of the structural formula 11

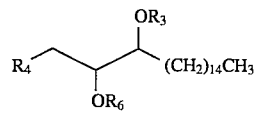

$R_6$ equals $CH_3SO_2$, $CF_3SO_2$ or p-$CH_3C_6H_4SO_2$ (11)

inverting 11 with azide ion to form a compound of the structural formula 12

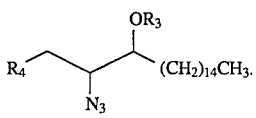 (12)

* * * * *

UNITED STATES PATENT AND TRADEMARK OFFICE
CERTIFICATE OF CORRECTION

PATENT NO. : 5,587,494
DATED : Dec. 24, 1996
INVENTOR(S) : Panzica, Raymond P. et al.

It is certified that error appears in the above-indentified patent and that said Letters Patent is hereby corrected as shown below:

On title page, in the formula, Structure 11, "OH" should read -- $OR_6$ --;

In the drawings, Structure 11, "OH" should read -- $OR_6$ --;

Column 1, line 45, "Sphinganine, 1" should read -- Sphingosine, 1 --

Signed and Sealed this

Twelfth Day of August, 1997

*Attest:*

*Attesting Officer*

BRUCE LEHMAN

*Commissioner of Patents and Trademarks*